US009585690B2

(12) United States Patent
Okoniewski

(10) Patent No.: US 9,585,690 B2
(45) Date of Patent: Mar. 7, 2017

(54) SURGICAL ACCESS DEVICE INCLUDING UNIVERSAL SEAL MECHANISM ASSOCIATED WITH BELLOWS

(71) Applicant: Covidien LP, Mansfield, MA (US)

(72) Inventor: Gregory G. Okoniewski, North Haven, CT (US)

(73) Assignee: Covidien LP, Mansfield, MA (US)

( * ) Notice: Subject to any disclaimer, the term of this patent is extended or adjusted under 35 U.S.C. 154(b) by 253 days.

(21) Appl. No.: 14/156,567

(22) Filed: Jan. 16, 2014

(65) Prior Publication Data

US 2014/0235953 A1    Aug. 21, 2014

Related U.S. Application Data

(60) Provisional application No. 61/767,350, filed on Feb. 21, 2013.

(51) Int. Cl.
*A61B 1/32* (2006.01)
*A61B 17/34* (2006.01)

(52) U.S. Cl.
CPC .. *A61B 17/3462* (2013.01); *A61B 2017/3464* (2013.01)

(58) Field of Classification Search
CPC ........ A61B 17/0293; A61B 2017/0287; A61B 17/17; A61B 2017/3464
USPC ................. 600/206, 215, 216, 233, 201–241
See application file for complete search history.

(56) References Cited

U.S. PATENT DOCUMENTS

| | | | |
|---|---|---|---|
| 5,634,908 A | 6/1997 | Loomas | |
| 7,169,130 B2 | 1/2007 | Exline et al. | |
| 7,740,598 B2 | 6/2010 | Heske et al. | |
| 7,833,200 B2 | 11/2010 | Viola | |
| 8,007,472 B2 | 8/2011 | Exline et al. | |
| 8,021,339 B2 | 9/2011 | Rockrohr et al. | |
| 2007/0255218 A1* | 11/2007 | Franer | A61B 17/3462 604/167.02 |
| 2008/0287877 A1 | 11/2008 | Gresham et al. | |
| 2010/0081880 A1* | 4/2010 | Widenhouse | A61B 17/3462 600/201 |
| 2010/0241082 A1 | 9/2010 | Taylor et al. | |

* cited by examiner

*Primary Examiner* — Mary Hoffman
*Assistant Examiner* — Tara R Carter

(57) ABSTRACT

A surgical access instrument for permitting access to body tissue is presented including a housing having a proximal end and a distal end, and a cannula member connected to the housing, the cannula member defining a longitudinal axis and permitting passage of a surgical object therethrough. The surgical access instrument also includes a sealing member disposed within the housing and including at least one opening therethrough, the sealing member configured to be connected to a plurality of bellows members extending in a vertical plane within the housing. The sealing member is also enabled to be displaced in a horizontal plane with respect to the longitudinal axis defined by the cannula member. Displacement of the sealing member in the horizontal plane is enabled by a roller assembly circumferentially arranged at the proximal end of the housing.

17 Claims, 16 Drawing Sheets

SURGICAL ACCESS DEVICE INCLUDING UNIVERSAL SEAL MECHANISM ASSOCIATED WITH BELLOWS

CROSS-REFERENCE TO RELATED APPLICATIONS

This application claims the benefit of and priority to U.S. Provisional Patent Application No. 61/767,350, filed Feb. 21, 2013, the entire disclosure of which is incorporated by reference herein.

BACKGROUND

Technical Field

The present disclosure relates to a seal system adapted to permit the introduction of surgical instrumentation into a patient's body. In particular, the present disclosure relates to a seal system for use with an introducer or access device, which is intended for insertion into a patient's body, and to receive an instrument in sealing engagement therewith.

Background of Related Art

Minimally invasive and laparoscopic procedures generally require that any instrumentation inserted into the body is sealed, i.e., provisions must be made to ensure that gases and/or fluids do not enter or exit the body through an endoscopic incision, such as, for example in surgical procedures where the surgical region is insufflated. For such procedures, the introduction of a tube into anatomical cavities, such as the peritoneal cavity, is usually accomplished by use of a system incorporating a trocar and cannula assembly. Since the cannula is in direct communication with the interior of the peritoneal cavity, insertion of the cannula into an opening in the patient's body to reach the inner abdominal cavity should be adapted to maintain a fluid tight interface between the abdominal cavity and the outside atmosphere.

In view of the need to maintain the atmospheric integrity of the inner area of the cavity, a seal assembly for a cannula, which permits introduction of a wide range of surgical instrumentation and maintains the atmospheric integrity of the inner area of the cavity, is desirable. In this regard, there have been a number of attempts in the prior art to achieve such sealing requirements. A difficulty encountered with conventional seal assemblies, however, is the inability of accommodating the wide range of sizes of instrumentation. In addition, angulation and/or manipulation of instrumentation within the cannula often present difficulties with respect to maintaining seal integrity.

SUMMARY

The following presents a simplified summary of the claimed subject matter in order to provide a basic understanding of some aspects of the claimed subject matter. This summary is not an extensive overview of the claimed subject matter. It is intended to neither identify key or critical elements of the claimed subject matter nor delineate the scope of the claimed subject matter. Its sole purpose is to present some concepts of the claimed subject matter in a simplified form as a prelude to the more detailed description that is presented later.

According to one aspect of the present disclosure, a surgical access instrument is provided for accessing body tissue. The surgical access instrument includes a housing having a proximal end and a distal end and a cannula member connected to the housing, the cannula member defining a longitudinal axis and permitting passage of a surgical object therethrough. The surgical access instrument also includes a sealing member disposed within the housing and including at least one opening therethrough, the sealing member configured to be connected to a plurality of bellows members extending in a vertical plane within the housing and the sealing member enabled to be displaced in a horizontal plane with respect to the longitudinal axis defined by the cannula member.

In one exemplary embodiment, displacement of the sealing member in the horizontal plane is enabled by a roller assembly circumferentially arranged at the proximal end of the housing. The roller assembly is configured to include a first series of rollers circumferentially disposed on an inner rim of the housing and a second series of rollers circumferentially disposed on an outer rim of the housing, such that the first and second series of rollers cooperate to advance the sealing member.

In another exemplary embodiment, the first series of rollers are equally spaced apart from each other across a circumference of the inner rim of the proximal end of the housing and the second series of rollers are equally spaced apart from each other across a circumference of the outer rim of the proximal end of the housing. The first series of rollers are disposed in opposed relation to the second series of rollers.

In yet another exemplary embodiment, when the sealing member shifts in the horizontal plane, uneven displacement is caused to the plurality of bellows members circumferentially disposed within the housing.

In another exemplary embodiment, when a portion of the plurality of bellows members are expanded on one end of the housing, a portion of the plurality of bellows members on an opposed end of the housing are contracted.

In yet another exemplary embodiment, each of the plurality of bellows members advance in a vertical direction with respect to the housing and cannula member when the surgical object is passed through the sealing member to cause off-axis movement thereof.

Each of the plurality of bellows members is biased to expand and/or contract based on the displacement of the sealing member in the horizontal plane when the surgical object is passed therethrough to cause off-axis movement of the sealing member. When the surgical object is removed from the at least one opening of the sealing member, the at least one opening of the sealing member and the plurality of bellows members assume an initial unbiased position.

In another exemplary embodiment, the distal end of the housing includes a duckbill seal configuration. The duckbill seal configuration includes at least one slit for receiving the surgical object therethrough and maintaining the surgical object substantially parallel with respect to the longitudinal axis defined by the cannula member.

In another exemplary embodiment, the sealing member is an elastomeric seal.

In another aspect of the present disclosure, a method of accessing body tissue during a surgical procedure is provided. The method includes the steps of providing a surgical access instrument including a housing having a proximal end and a distal end; a cannula member connected to the housing, the cannula member defining a longitudinal axis and permitting passage of a surgical object therethrough; and a sealing member disposed within the housing and including at least one opening therethrough, the sealing member configured to be connected to a plurality of bellows members extending in a vertical plane within the housing and the sealing member enabled to be displaced in a horizontal plane with respect to the longitudinal axis defined by the cannula member. The method also includes the steps of inserting the surgical access instrument through an incision, introducing the surgical object through the surgical access instrument, and performing at least one surgical task with the surgical object.

Further scope of applicability of the present disclosure will become apparent from the detailed description given hereinafter. However, it should be understood that the detailed description and specific examples, while indicating preferred embodiments of the present disclosure, are given by way of illustration only, since various changes and modifications within the spirit and scope of the present disclosure will become apparent to those skilled in the art from this detailed description.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

Figure 1:
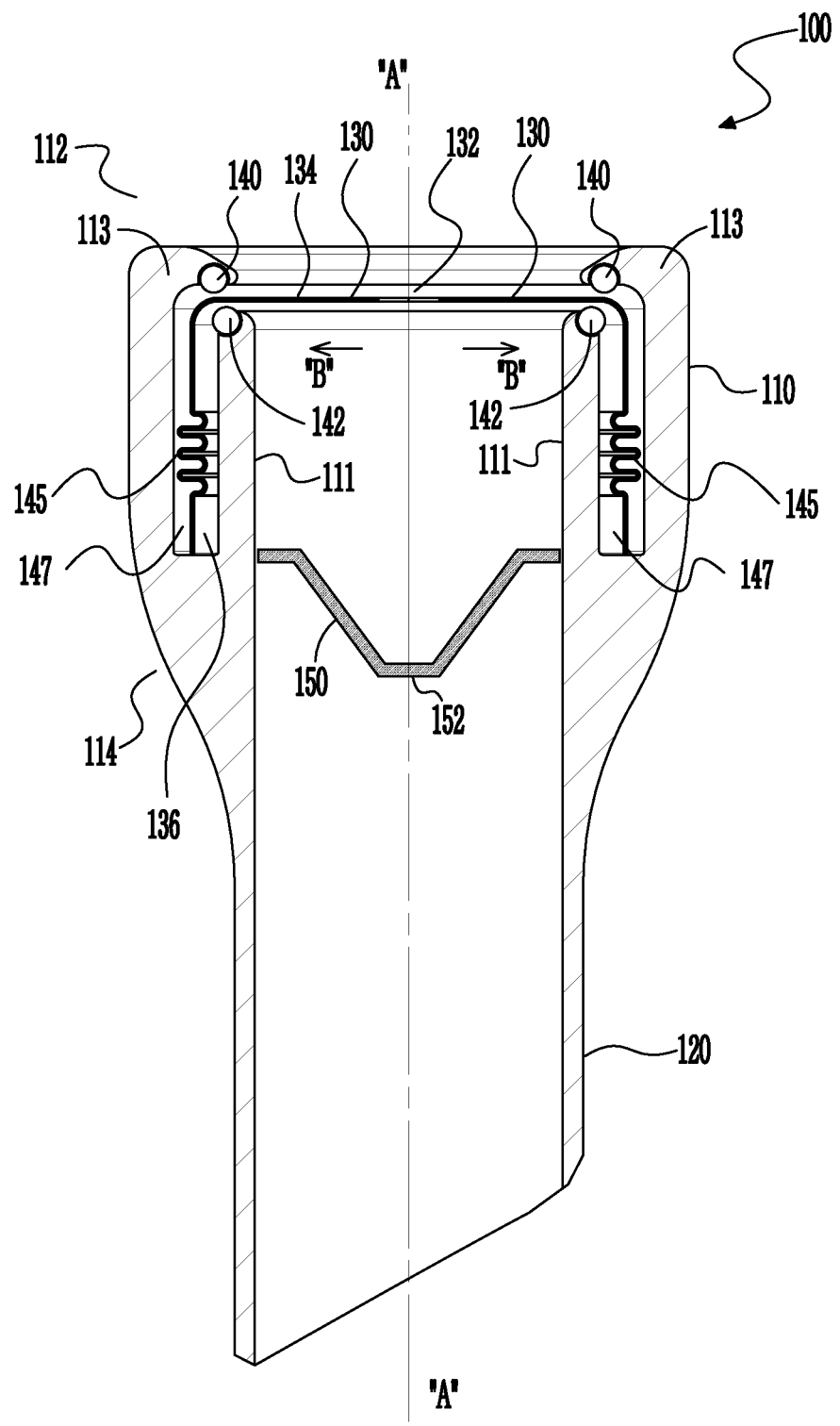
FIG. 1 is a side, cross-sectional view of a cannula assembly and a seal assembly, the cannula assembly having a plurality of rollers and the seal assembly illustrating an opening thereon, in accordance with the present disclosure.

The figures depict preferred embodiments of the present disclosure for purposes of illustration only. One skilled in the art will readily recognize from the following discussion that alternative embodiments of the structures and methods illustrated herein may be employed without departing from the principles of the present disclosure described herein.

DETAILED DESCRIPTION

Particular embodiments of the present disclosure are described hereinbelow with reference to the accompanying drawings. However, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

For the purposes of promoting an understanding of the principles of the present disclosure, reference will now be made to the exemplary embodiments illustrated in the drawings, and specific language will be used to describe the same. It will nevertheless be understood that no limitation of the scope of the present disclosure is thereby intended. Any alterations and further modifications of the inventive features illustrated herein, and any additional applications of the principles of the present disclosure as illustrated herein, which would occur to one skilled in the relevant art and having possession of this disclosure, are to be considered within the scope of the present disclosure.

The cannula assembly of the present disclosure, in combination with a seal system internal to the cannula assembly, provides a substantial seal between a body cavity of a patient and the outside atmosphere before, during and after insertion of a surgical instrument through the cannula assembly. Moreover, the seal assembly of the present disclosure is capable of accommodating surgical instruments of varying diameters, e.g., from 5 mm to 15 mm, by providing a gas tight seal with each instrument when inserted. The flexibility of the present seal assembly greatly facilitates endoscopic surgery where a variety of instruments having differing diameters are often needed during a single surgical procedure.

The seal assembly contemplates the introduction and manipulation of various types of instrumentation adapted for insertion through a trocar and/or cannula assembly while maintaining a fluid tight interface about the instrumentation to preserve the atmospheric integrity of a surgical procedure from gas and/or fluid leakage. Specifically, the seal assembly accommodates angular manipulation of the surgical instrument relative to the seal housing axis. This feature of the present disclosure desirably minimizes the entry and exit of gases and/or fluids to/from the body cavity. Examples of instrumentation include clip appliers, graspers, dissectors, retractors, staplers, laser probes, photographic devices, endoscopes and laparoscopes, tubes, and the like. Such instruments will be collectively referred to herein as "instruments or instrumentation."

Embodiments of the presently disclosed apparatus will now be described in detail with reference to the drawings, in which like reference numerals designate identical or corresponding elements in each of the several views. As used herein, the term "distal" refers to that portion of the tool, or component thereof which is further from the user while the term "proximal" refers to that portion of the tool or component thereof which is closer to the user.

Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

For exemplary purposes, the access apparatus will be described in terms of a cannula assembly, which is adapted for introduction, typically utilizing a trocar, within the abdominal cavity during a laparoscopic surgical procedure. However, it is appreciated that the access apparatus may be any apparatus suitable for introduction and passage of surgical objects into underlying tissue including, e.g., catheters, trocar assemblies, endoscopic portals, hand access devices, etc., through an incision or through a natural body opening.

Figure 2:
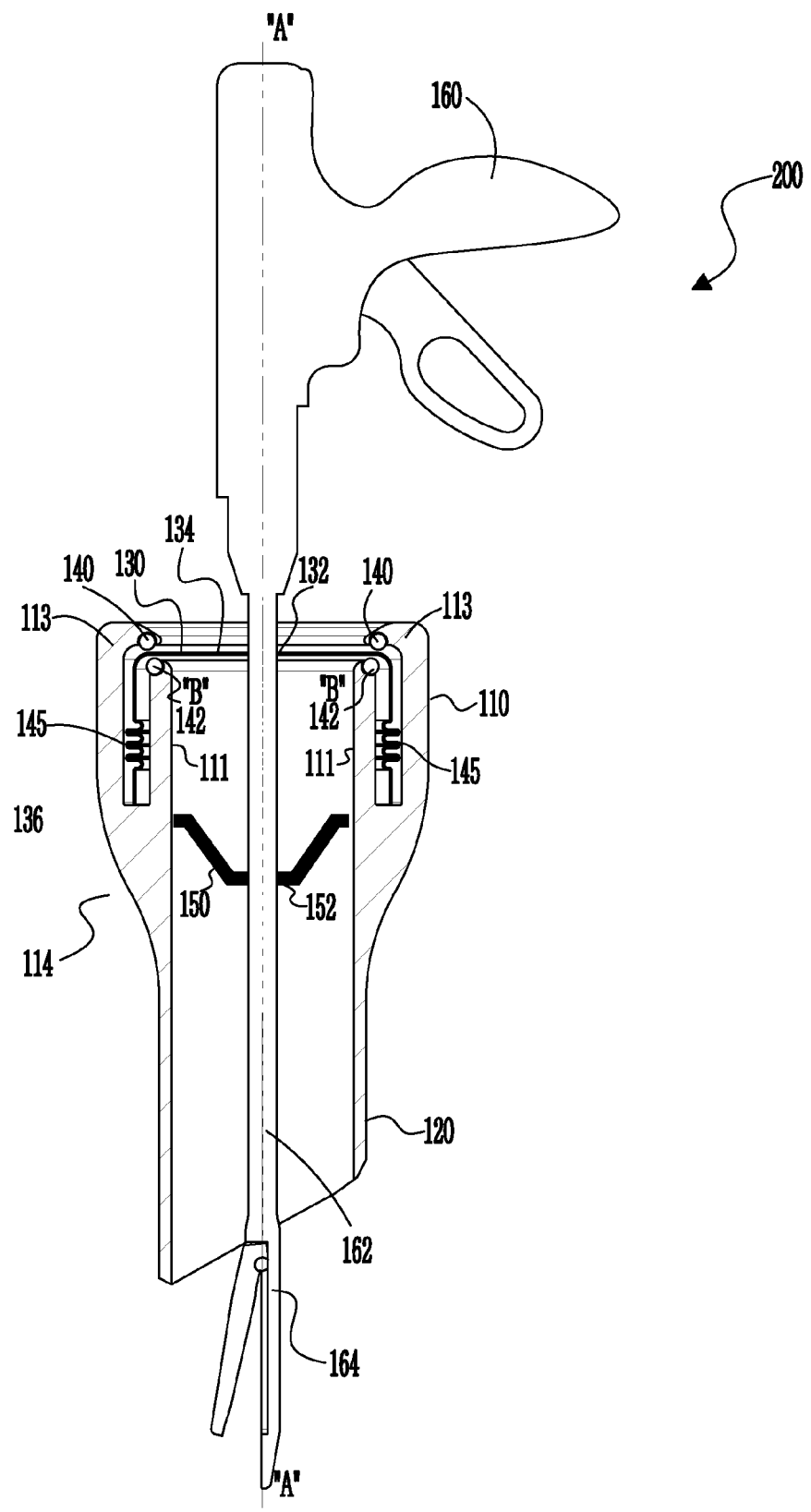
FIG. 2 is a side, cross-sectional view of the cannula assembly and the seal assembly of FIG. 1, where the seal receives at least one surgical instrument therethrough, in accordance with the present disclosure.

Referring now to the drawings, in which like reference numerals identify identical or substantially similar parts throughout the several views, FIGS. 1-2 illustrate a surgical access instrument 100. Surgical access instrument 100 may be any conventional cannula suitable for the intended purpose of accessing a body cavity and permit introduction of instruments therethrough. Surgical access instrument 100 is particularly adapted for use in laparoscopic surgery where the peritoneal cavity is insufflated with a suitable fluid, e.g., $CO_2$, to raise the cavity wall from the internal organs therein.

Surgical access instrument 100 includes cannula housing 110 and cannula member 120. Cannula housing 110 is mounted to a proximal end of the cannula member 120. Cannula member 120 defines a longitudinal axis "A" extending along the length of cannula member 120. Cannula member 120 further defines an internal longitudinal passage dimensioned to permit passage of surgical instrumentation (see FIG. 2), in a second configuration 200. Cannula member 120 may be formed of stainless steel or other rigid materials, such as a polymeric material or the like. Cannula member 120 may be clear or opaque. The diameter of cannula member 120 may vary, but typically ranges from 10 to 15 mm for use with the cannula housing 110 of the present disclosure.

A sealing member 130 is positioned at a proximal end 112 of the cannula housing 110. The sealing member 130 is used to maintain pressure for laparoscopic access and for other similar applications. The sealing member 130 may be an elastomeric seal. Alternatively, the sealing member 130 includes a fabric material, which includes a plurality of strands and an elastomeric material. The sealing member 130 is substantially flat in the horizontal plane where laparoscopic instruments are introduced through an orifice 132.

The sealing member 130 has an elongate shape extending along vertical cavities 147 of the cannula housing 110. The sealing member 130 has a proximal end 134 and a distal end 136. For example, the sealing member 130 may include first and second ends 134, 136 with the first end 136 (distal end) being secured to the distal end 114 of the cannula housing 110 at a first location along the vertical cavities 147. The second end 134 (proximal end) is adapted for axial movement in response to the passage of a surgical instrument 160 (see FIG. 2) through the sealing member 130.

The orifice 132 is disposed at a center-portion of the sealing member 130, where the sealing member 130 is in an unbiased position. In one exemplary embodiment, the center-portion is adapted to expand when receiving the surgical instrument 160. In one embodiment, the fabric material may include a plurality of monofilament strands and a plurality of multifilament strands.

The sealing member 130 is disposed within the cannula housing 110 and, in certain exemplary embodiments, is configured to be actuated by a roller assembly 140, 142 circumferentially arranged at the proximal end 112 of the cannula housing 110. The roller assembly 140, 142 is configured to include a first series of rollers 142 circumferentially disposed on an inner rim 111 of the cannula housing 110 and a second series of rollers 140 circumferentially disposed on an outer rim 113 of the cannula housing 110, such that the first and second series of rollers 140, 142 cooperate to advance the sealing member 130 in a direction "B." The sealing member 130 is preferably advanced in the horizontal direction (i.e., perpendicular to axis "A") when the surgical instrument 160 is received therethrough (see FIG. 2).

The first series of rollers 142 are equally spaced apart from each other across a circumference of the inner rim 111 of the proximal end 112 of the cannula housing 110. The second series of rollers 140 are equally spaced apart from each other across a circumference of the outer rim 113 of the proximal end 112 of the cannula housing 110. The first series of rollers 142 are disposed in opposed relation to the second series of rollers 140, such that the sealing member 130 frictionally engages the first and second series of rollers 140, 142 as it advances horizontally along the top portion of the cannula housing 110.

The sealing member 130 is configured to be connected to a plurality of bellows members 145. The plurality of bellows members 145 are disposed within cavities 147. The cavities 147 extend a length of the cannula housing 110. The cavities 147 may extend a portion of a length of the cannula housing 110. Alternatively, it is contemplated that the cavities 147 extend the entire length of the cannula housing 110. Therefore, motion is converted from the vertical to the horizontal direction, and vice versa, based on the series of rollers 140, 142 circumferentially arranged around the periphery or perimeter of the cannula housing 110.

In particular, the sealing member 130 advances from the vertical plane to a horizontal plane via the plurality of bellows members 145, the horizontal plane configured to be perpendicular to the longitudinal axis "A" defined by the cannula member 120. The plurality of bellows members 145 are placed or positioned within the vertical cavities 147. When the surgical instrument 160 is passed therethrough (see FIG. 2), the sealing member 130 and the plurality of bellows members 145 are retained in an unbiased position. The plurality of bellows members 145 allow the sealing member 130 to move horizontally with the surgical instrument 160 over a relatively small range, thus eliminating the influence of friction between the sealing member 130 and the surgical instrument 160 during manipulation of the surgical instrument 160 during a surgical procedure. Therefore, the plurality of bellows members 145, extending in the vertical direction in the vertical cavities 147 allow for horizontal movement and/or displacement of the sealing member 130 on the horizontal plane relative to the cannula housing 110 and the cannula member 120.

With further reference to FIGS. 1-2, cannula housing 110 further includes duck bill or zero closure valve 150, which tapers distally and inwardly to a sealed configuration as shown in the figure. Valve 150 opens to permit passage of the surgical instrumentation and closes in the absence of the instrumentation. When permitting passage of instrumentation, valve 150 includes an aperture 152 for receiving the instrumentation therethrough. Thus, the duckbill seal configuration 150 includes at least one slit or aperture 152 for receiving the surgical instrument 160 therethrough and maintaining the surgical instrument 160 substantially parallel with respect to the longitudinal axis "A" defined by the cannula member 120.

For example, as shown in FIG. 2, the shaft 162 of surgical instrument 160 is secured at aperture 152 of valve 150, whereas the end effector 164 of the surgical instrument 160 extends beyond the distal end of the cannula member 120 to expose the end effector 164 within the body cavity. Valve 150 is preferably adapted to close upon exposure to the forces exerted by the insufflation gases in the internal cavity, as the various portions of the surgical instrument 160 are passed therethrough. Other zero closure valves are also contemplated including single or multiple slit valve arrangements, trumpet valves, flapper valves, etc.

Referring back to FIG. 1, cannula housing 110 is integrated with cannula member 120, which was previously introduced into an insufflated abdominal cavity. A surgical instrument 160 is inserted into cannula housing 110 through passage 132 of the sealing member 130. If the axis of the surgical instrument 160 is not perfectly aligned with the axis "A" of cannula member 120, then the surgical instrument 160 contacts the inner walls and/or the inner surfaces of cannula member 120. Contact with the cannula member 120 may cause some slight deformation of the sealing member 130. The surgical instrument 160 passes further distally into the cannula member 120 passing through duckbill valve 150. The surgical instrument 160 slides along the surface of the cannula member 120, through the duckbill valve 150 to the aperture 152. Aperture 152 stretches to accommodate the instrument diameter, as necessary. The sealing member 130 maintains sealing engagement with the surgical instrument 160 passed therethrough. Preferably, the sealing member 130 includes resilient material and fabric material, which resists deformation of aperture 152, as well as tearing of sealing member 130.

In operation or use, as the surgical instrument 160 is moved left and right and substantially perpendicular to axis "A," (or at an angle with respect to axis "A") bellows members 145 are expanded/contracted in the vertical cavities 147 in response to movement/displacement of the sealing member 130. When the surgical instrument 160 is removed from the cannula member 120 and the cannula housing 110, bellows members 145 may re-position the sealing member 130 back to its centered and unbiased position. The unbiased position is a substantially central position with respect to axis "A," as illustrated in FIG. 1. Thus, bellows members 145 may act to negate the displacement caused by the insertion of one or more surgical instruments through the cannula housing 110 and the sealing member 130. Stated differently, sealing member 130 is re-positioned to its initial unbiased position, where the sealing member 130 is coaxial with axis "A" defined by the cannula housing 110 and the cannula member 120. Additionally, bellows members 145 may secure the sealing member 130 to prevent rotation or swiveling of the surgical instrument 160. Stated differently, bellows members 145 keep or maintain the sealing member 130 taut when surgical instruments are inserted through orifice 132 of sealing member 130, in order to prevent insufflation gasses from escaping.

With reference to FIGS. 3A-3D, a top perspective view of the cannula, housing, and seal assemblies 110, 120, 130 illustrating the movement of the sealing member 130 with respect to the first and second series of rollers 140, 142 is depicted.

FIGS. 3A-3D illustrate that when the sealing member 130 shifts in the horizontal plane, uneven displacement is caused to the plurality of bellows members 145 circumferentially disposed within the housing 110. In other words, when a portion of the plurality of bellows members 145 are expanded on one end of the housing 110, a portion of the plurality of bellows members 145 on an opposed end of the housing 110 are contracted.

In other words, each of the plurality of bellows members 145 advance in a vertical direction (within cavities 147) with respect to the housing 110 and cannula member 120 when the surgical object 160 is passed through the sealing member 130 to cause off-axis movement thereof. Stated differently, each of the plurality of bellows members 145 is biased to expand and/or contract based on the displacement of the sealing member 130 in the horizontal plane when the surgical object 160 is passed therethrough to cause off-axis movement of the sealing member 130. When the surgical object 160 is removed from the at least one opening 132 of the sealing member 130, the at least one opening 132 of the sealing member 130 and the plurality of bellows members 145 once again automatically assume an initial unbiased position.

Figure 3A:
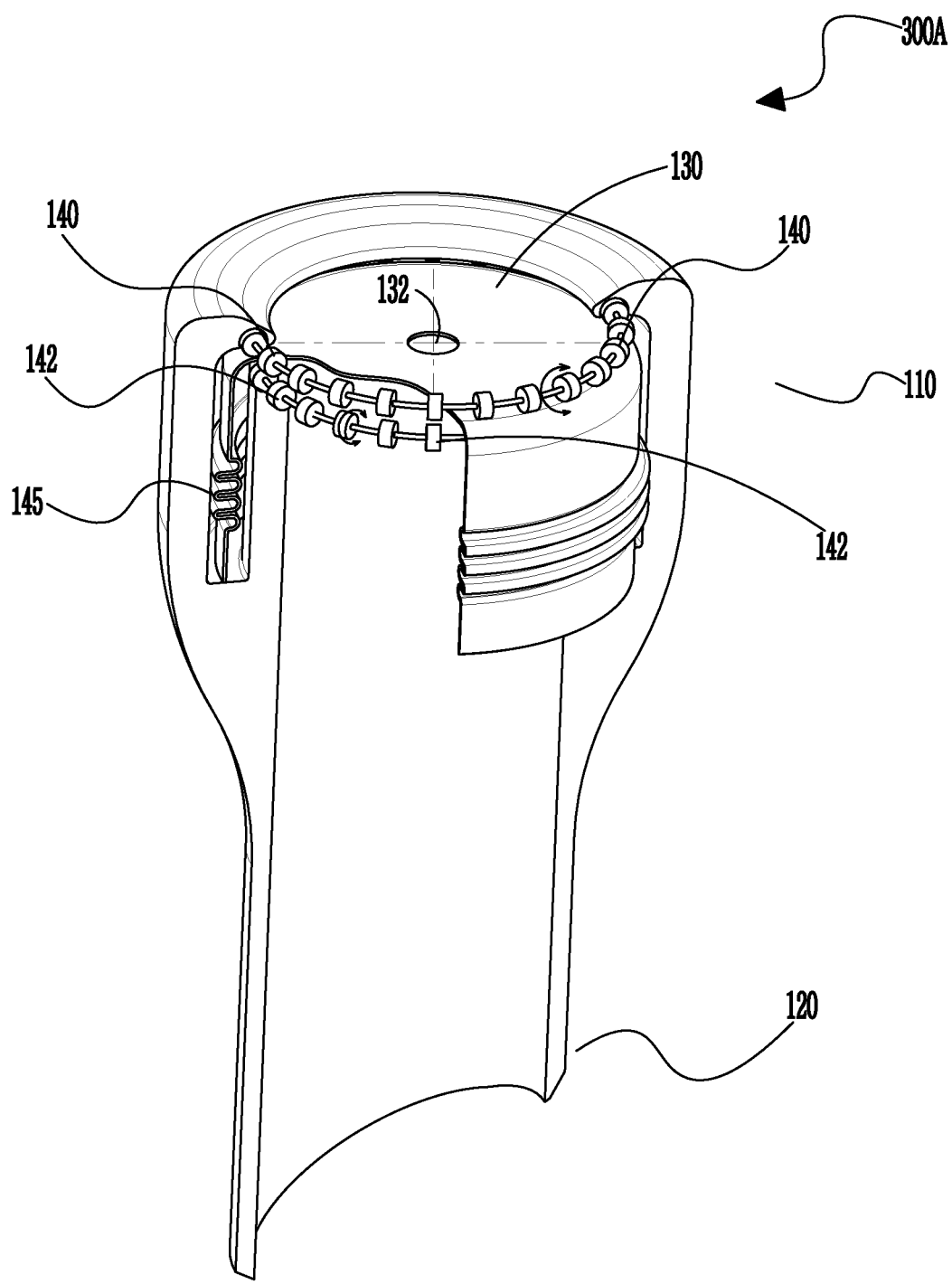
FIG. 3A is a top perspective, partially cut-away view of the cannula and seal assemblies illustrating the seal with respect to the series of rollers in an unbiased position, in accordance with an embodiment of the present disclosure.
Figure 3B:
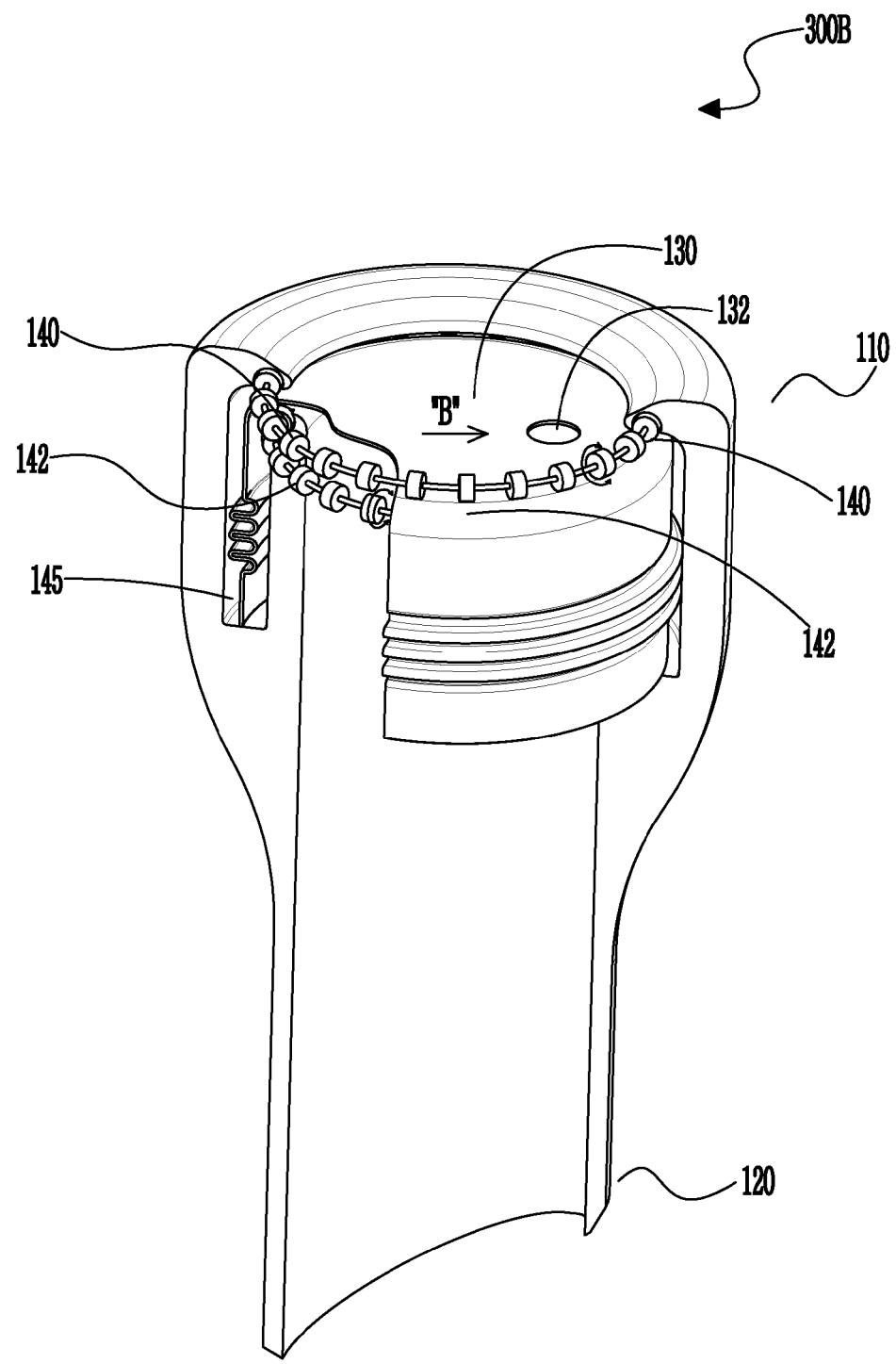
FIG. 3B is a top perspective, partially cut-away view of the cannula and seal assemblies illustrating the movement of the seal with respect to the series of rollers, where the seal has moved to the right and the left bellows members have expanded in response to such movement, in accordance with an embodiment of the present disclosure.
Figure 3C:
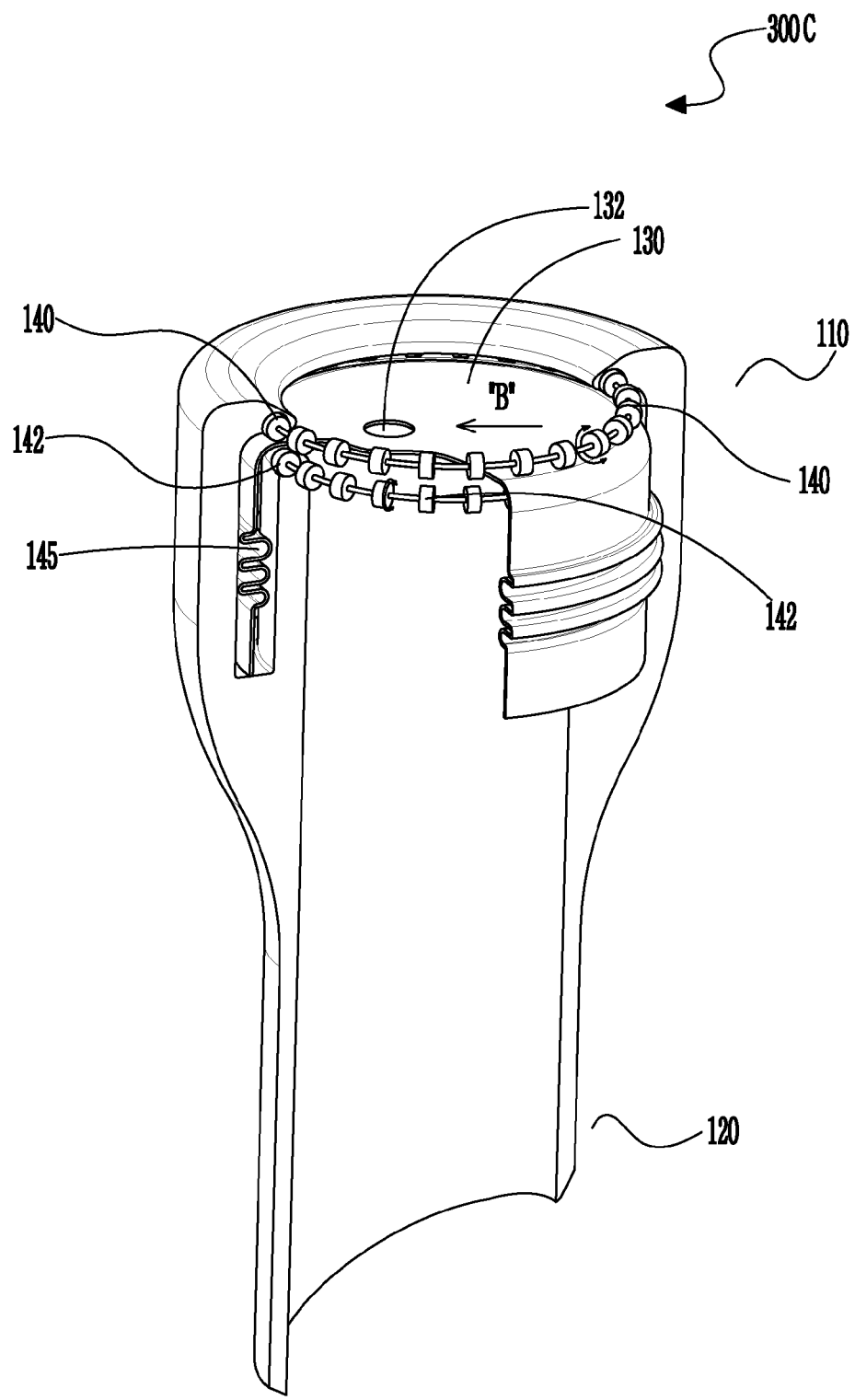
FIG. 3C is a top perspective, partially cut-away view of the cannula and seal assemblies illustrating the movement of the seal with respect to the series of rollers, where the seal has moved to the left and the right bellows members have contracted in response to such movement, in accordance with an embodiment of the present disclosure.
Figure 3D:
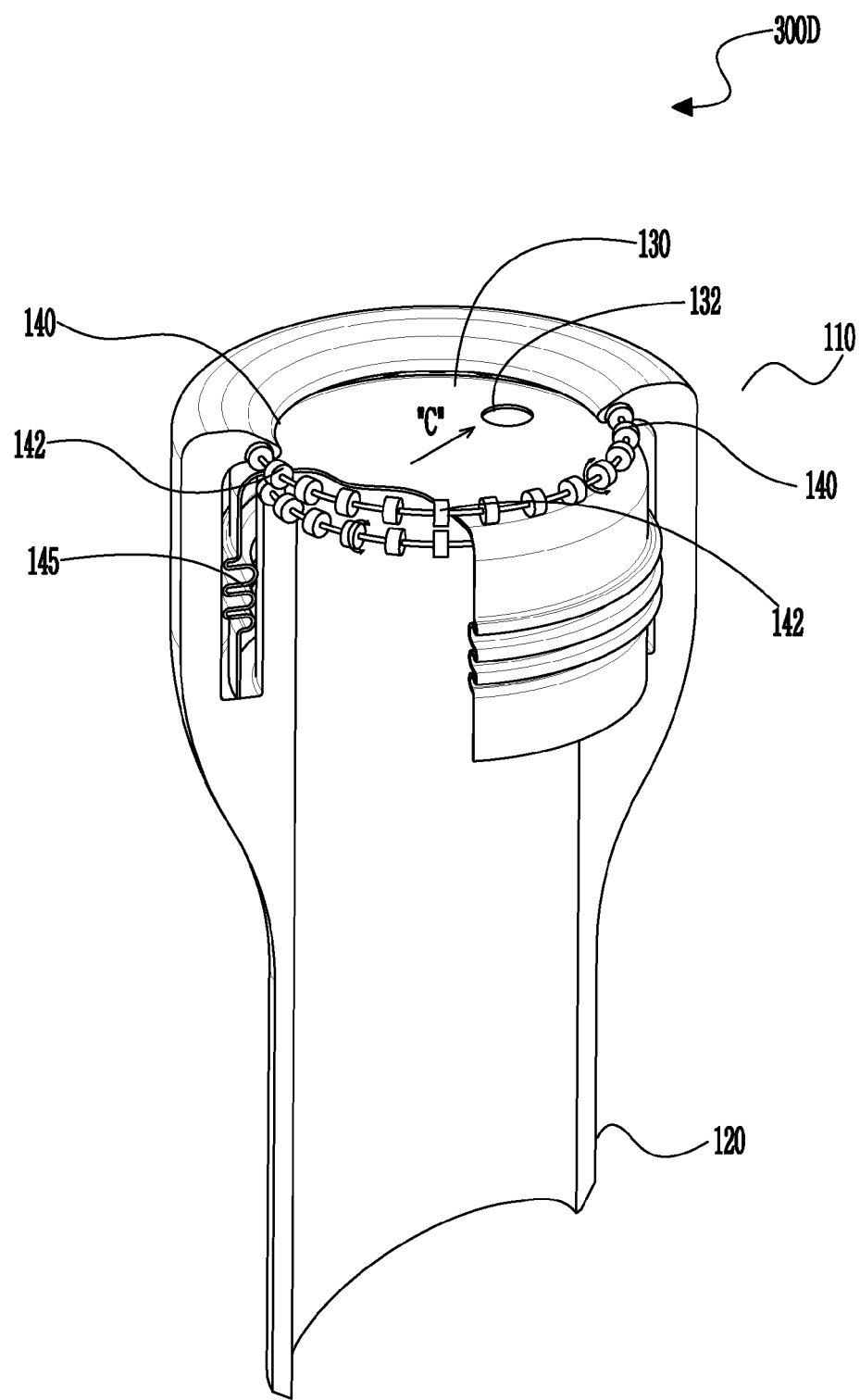
FIG. 3D is a top perspective, partially cut-away view of the cannula and seal assemblies illustrating the movement of the seal with respect to the series of rollers, where the seal has moved diagonally and the left bellows members have expanded in response to such movement, in accordance with an embodiment of the present disclosure.
Figure 4A:
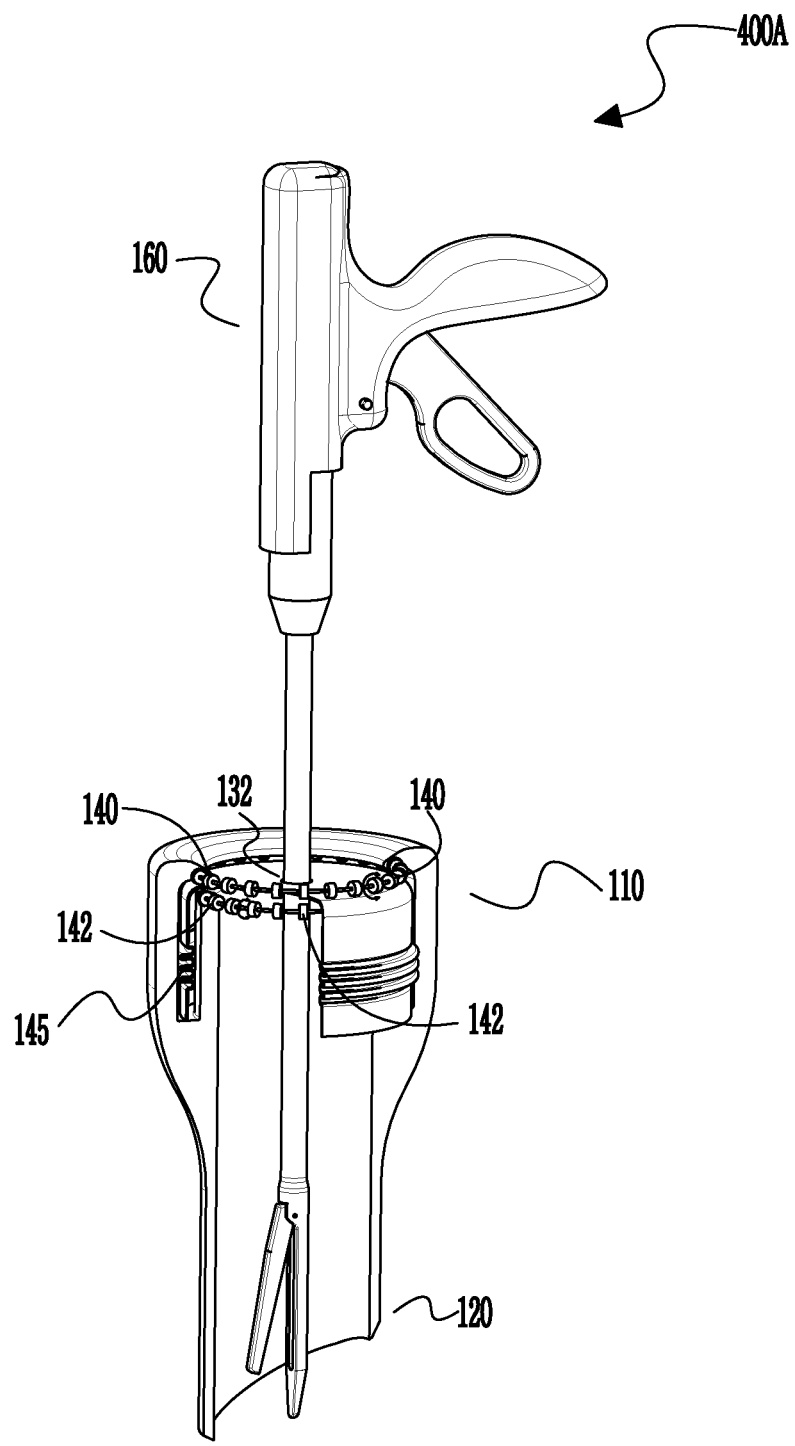
FIG. 4A is a top perspective, partially cut-away view of the cannula and seal assemblies illustrating the seal with respect to the series of rollers in an unbiased position, when a surgical instrument has been inserted therethrough, in accordance with an embodiment of the present disclosure.
Figure 4B:
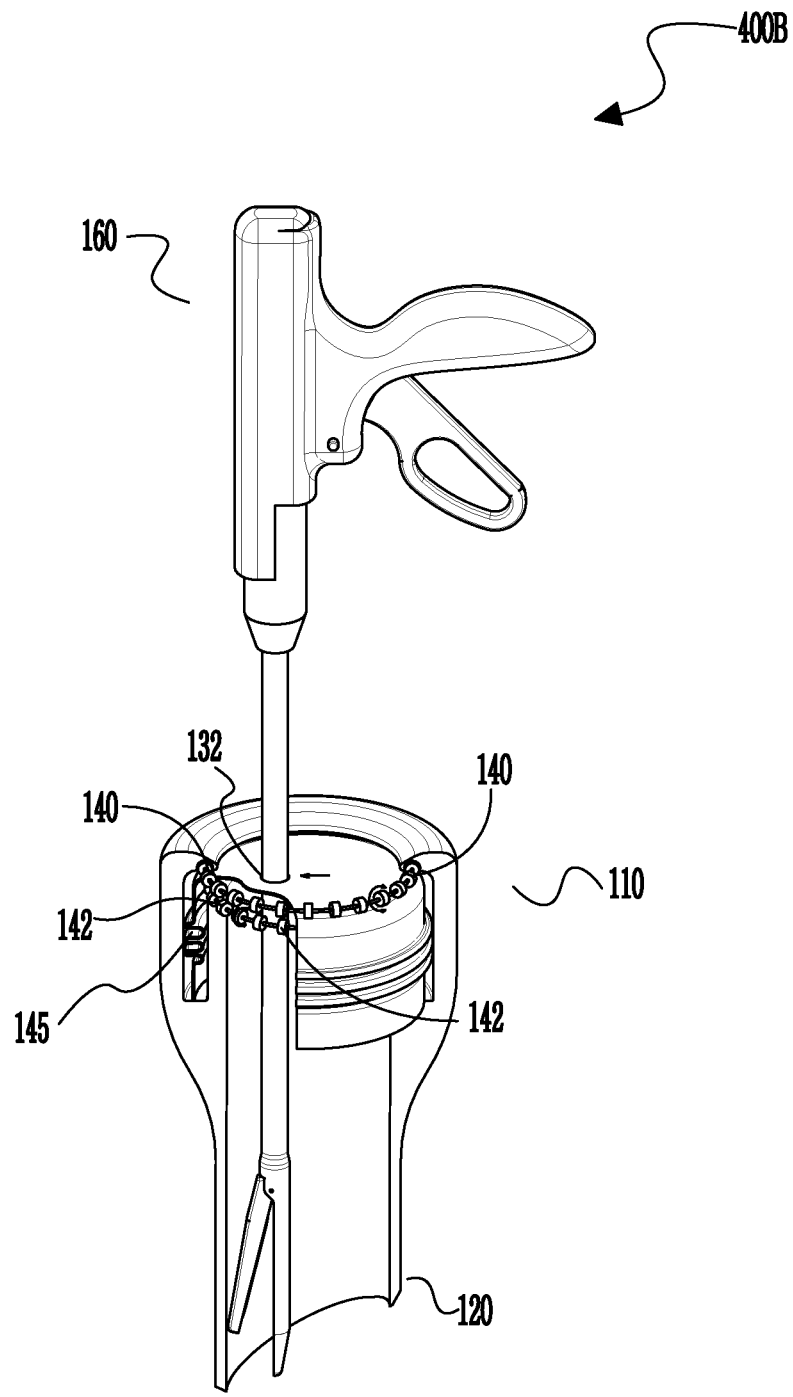
FIG. 4B is a top perspective, partially cut-away view of the cannula and seal assemblies illustrating the movement of the seal with respect to the series of rollers, when a surgical instrument has been inserted therethrough, where the seal has moved to the right and the left bellows members have expanded in response to such movement, in accordance with an embodiment of the present disclosure.
Figure 4C:
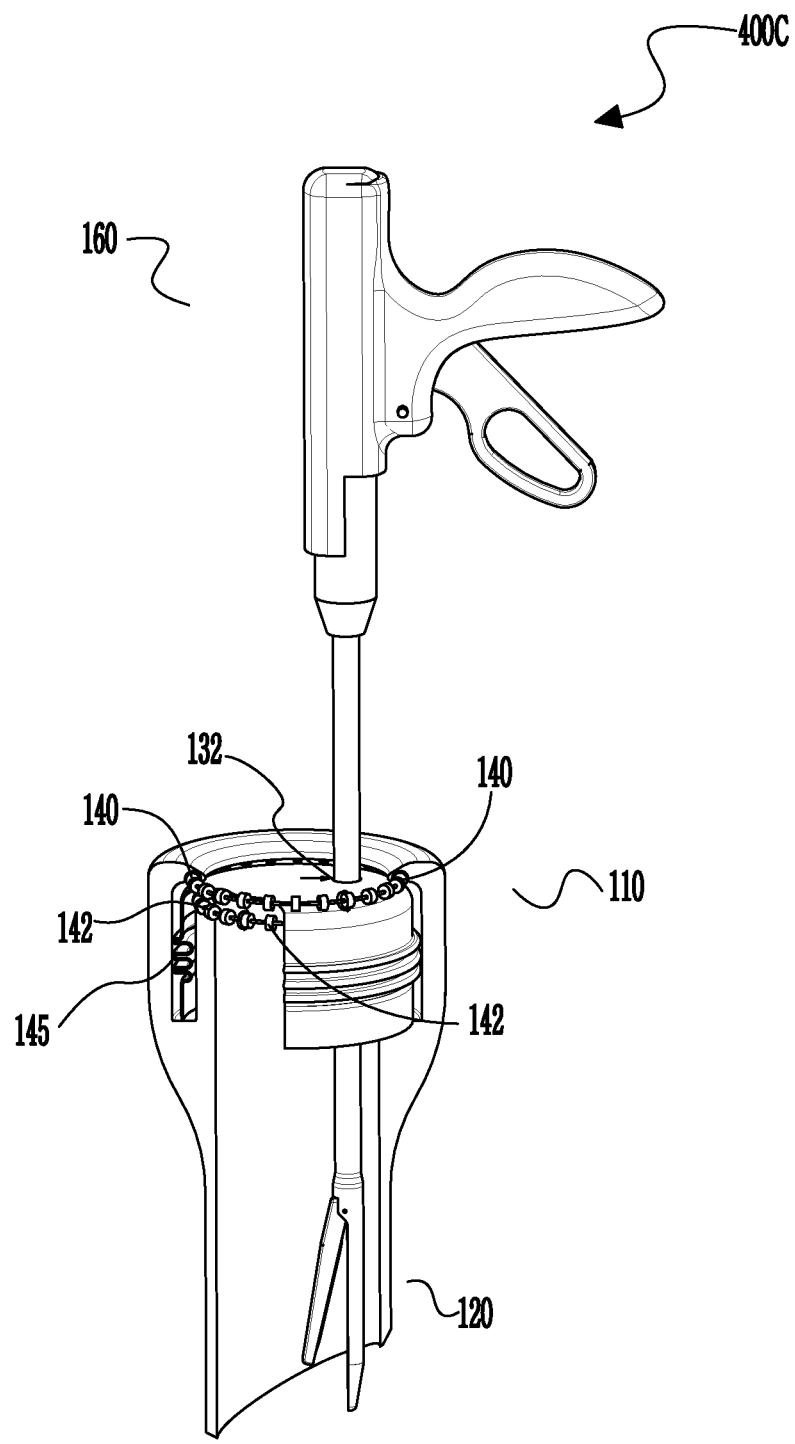
FIG. 4C is a top perspective, partially cut-away view of the cannula and seal assemblies illustrating the movement of the seal with respect to the series of rollers, when a surgical instrument has been inserted therethrough, where the seal has moved to the left and the right bellows members have contracted in response to such movement, in accordance with an embodiment of the present disclosure.
Figure 4D:
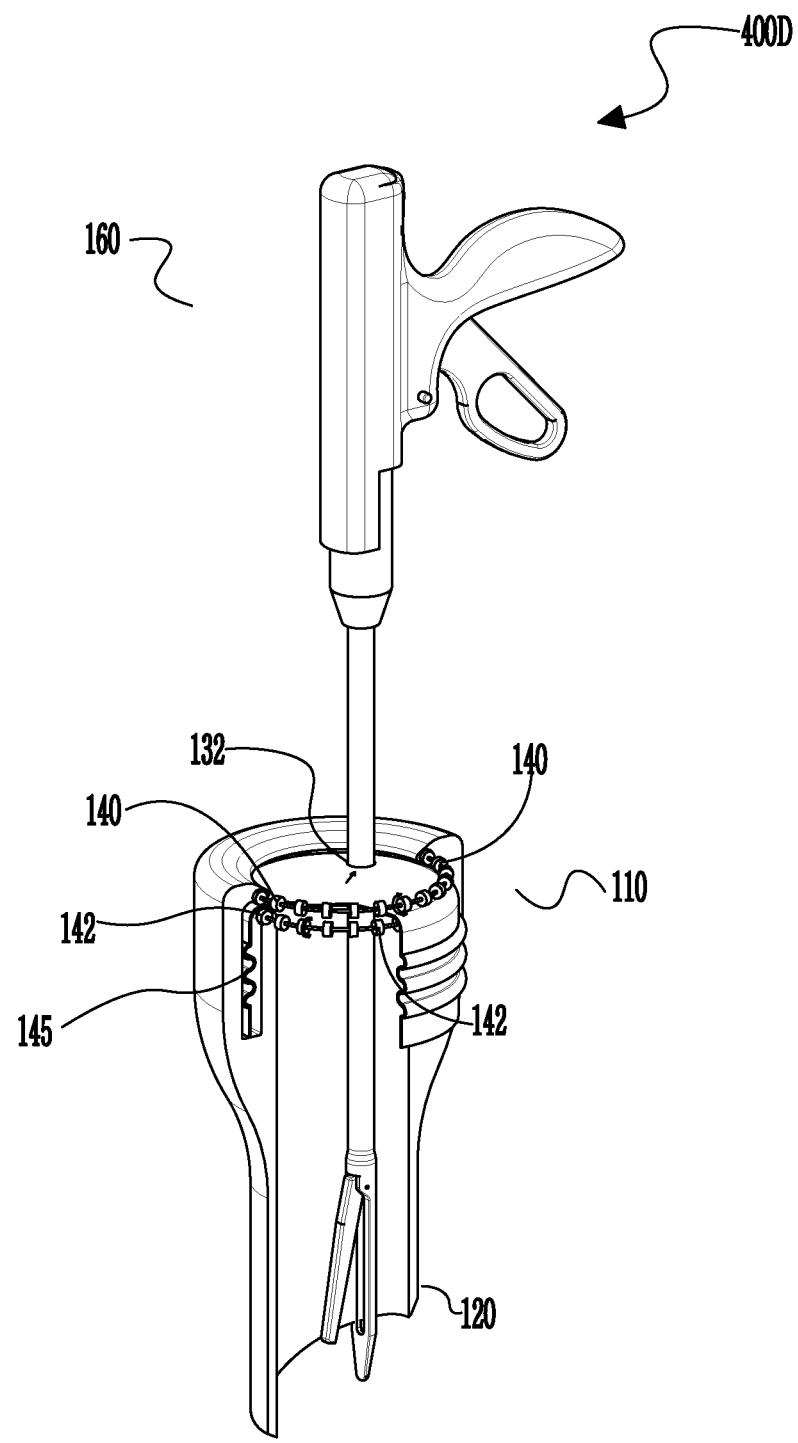
FIG. 4D is a top perspective, partially cut-away view of the cannula and seal assemblies illustrating the movement of the seal with respect to the series of rollers, when a surgical instrument has been inserted therethrough, where the seal has moved diagonally and the left bellows members have expanded in response to such movement, in accordance with an embodiment of the present disclosure.

For example, in FIG. 3A, in a first configuration 300A, the opening 132 is shown in an unbiased, substantially central position. The plurality of bellows members 145 are also unbiased. In FIG. 3B, in a second configuration 300B, the opening 132 of the sealing member 130 has been shifted to the right, in the direction "B." Therefore, the sealing member 130 is in a biased position. Thus, the plurality of bellows members 145 on the left portion of the housing 110 are shown expanded with respect to their unbiased position in FIG. 3A. In FIG. 3C, in a third configuration 300C, the opening 132 of the sealing member 130 has been shifted to the left, in the direction "B." Therefore, the sealing member 130 is in a biased position. Thus, the plurality of bellows members 145 on the right portion of the housing 110 are expanded with respect to their unbiased position, whereas the plurality of bellows members 145 on the left portion of the housing 110 are contracted with respect to their unbiased position in FIG. 3A. Similarly, in FIG. 3D, in a fourth configuration 300D, the opening 132 of the sealing member 130 has been shifted in a diagonal direction, in the direction "C." Therefore, the sealing member 130 is in a biased position. Thus, the plurality of bellows members 145 on the right portion of the housing 110 are contracted with respect to their unbiased position, whereas the plurality of bellows members 145 on the left portion of the housing 110 are expanded with respect to their unbiased position in FIG. 3A. Consequently, a direct relationship is established between the expansion/contraction of the plurality of bellows members 145 and the movement/displacement of the sealing member 130. The more the opening 132 of the sealing member 130 is set off-axis to the center, unbiased position, the larger the expansion/contraction of the plurality of bellows members 145 circumferentially disposed around the housing 110. It is contemplated that the opening 132 of the sealing member 130 may be displaced in any direction and up to the edge of the top portion of the housing 110.

FIGS. 4A-4D, merely illustrate the surgical instrument 160 inserted through the opening 132 of the sealing member 130 of FIGS. 3A-3D, respectively. In other words, the first configuration 400A depicts the surgical instrument 160 inserted therethrough when the opening 132 of the sealing member 130 is in the unbiased position, whereas the second, third, and fourth configurations 400B, 400C, and 400D depict the opening 132 of the sealing member 130 in a variety of biased positions (left, right, and diagonal). Therefore, as the surgical instrument 160 is displaced or moved laterally or horizontally across the length of the sealing member 130, the plurality of bellows members 145 expand/contract in response to such movement. For instance, when a first portion/section expands, a second opposed portion/section contracts in equal, but opposed lengths or distances. Additionally, when the surgical instrument 160 is removed from the opening 132 of the sealing member 130, the plurality of bellows members 145 are pre-loaded to enable the automatic repositioning of the sealing member to its natural, unbiased position (which is substantially centrally disposed with respect to the top position of the housing 110).

Figure 5:
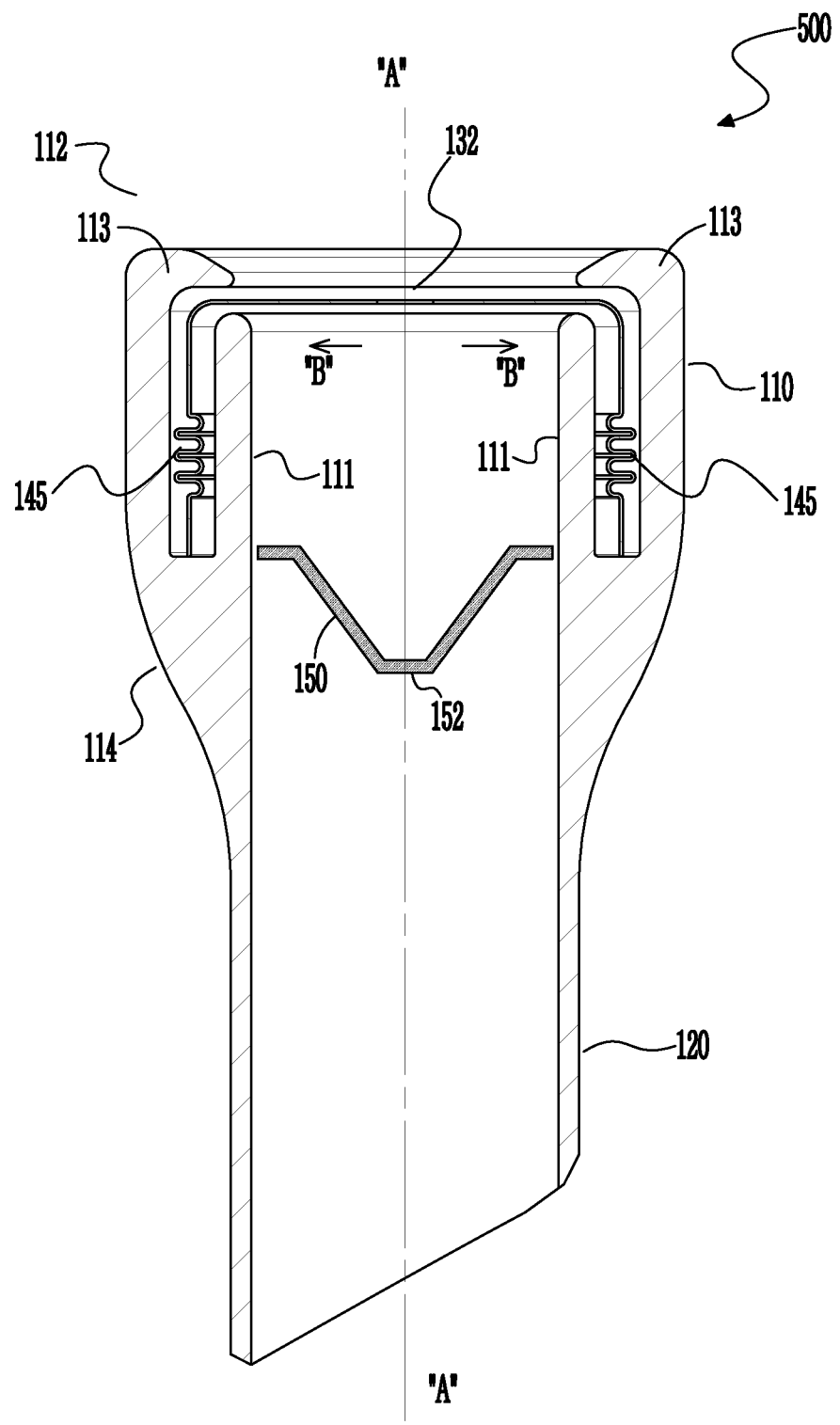
FIG. 5 is a side, cross-sectional view of a cannula assembly and a seal assembly, with a plurality of bellows members and no rollers, in accordance with the present disclosure.
Figure 6:
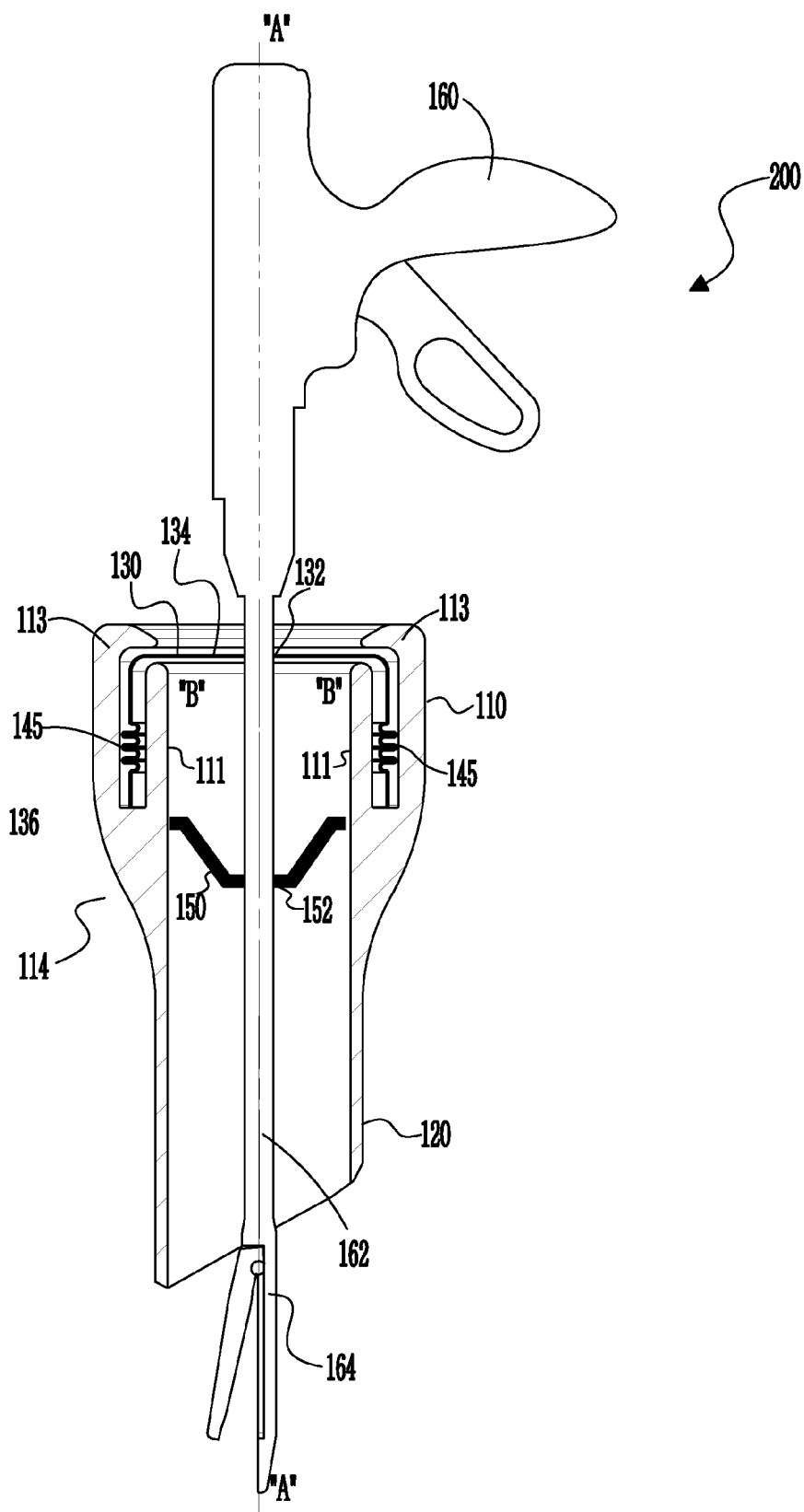
FIG. 6 is a side, cross-sectional view of the cannula assembly and the seal assembly of FIG. 5, where the sealing member receives at least one surgical instrument therethrough, without biasing the sealing member, in accordance with the present disclosure.
Figure 7A:
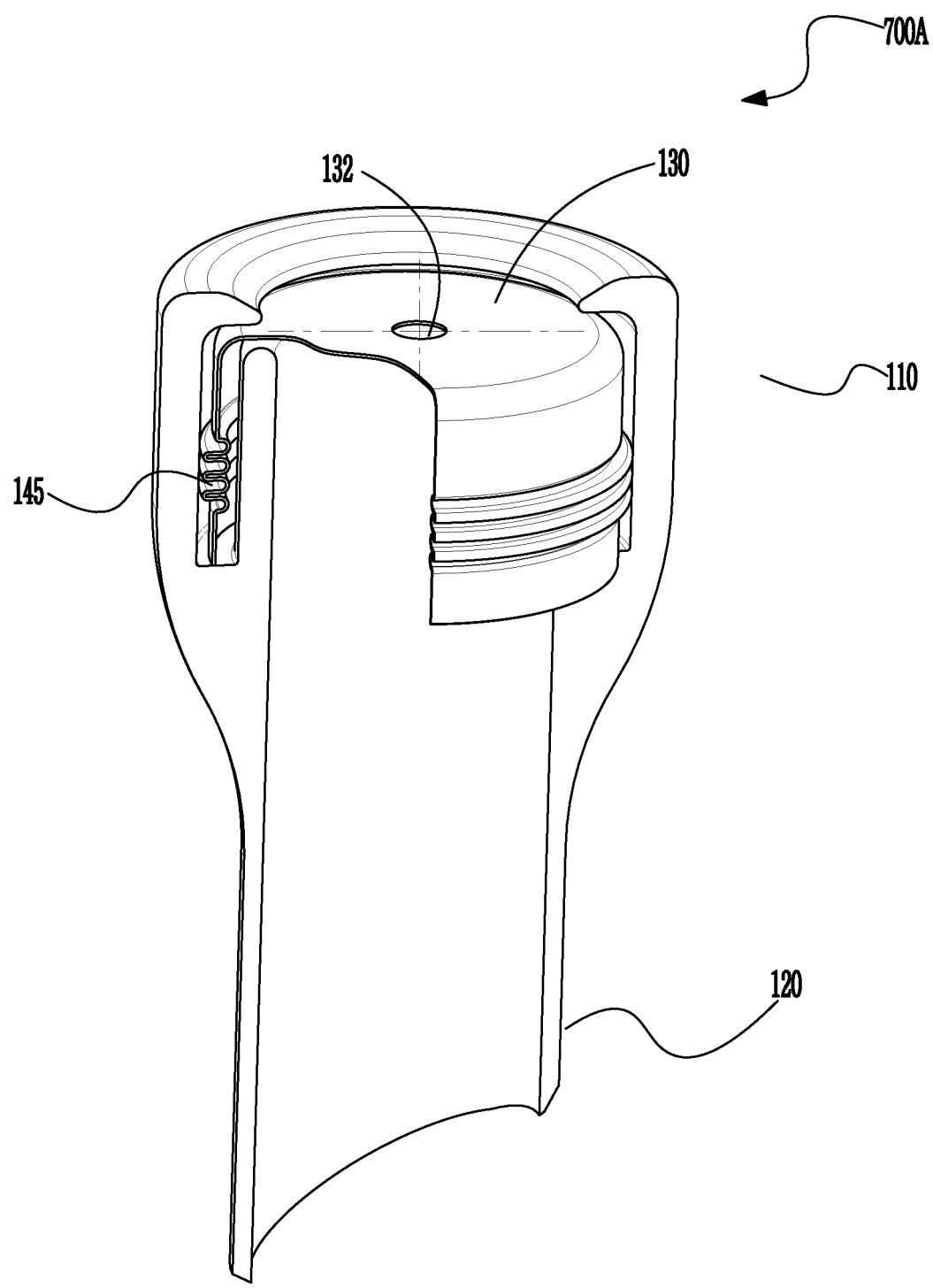
FIG. 7A is a top perspective, partially cut-away view of the cannula and seal assemblies illustrating the sealing member with no rollers, in accordance with an embodiment of the present disclosure.
Figure 7B:
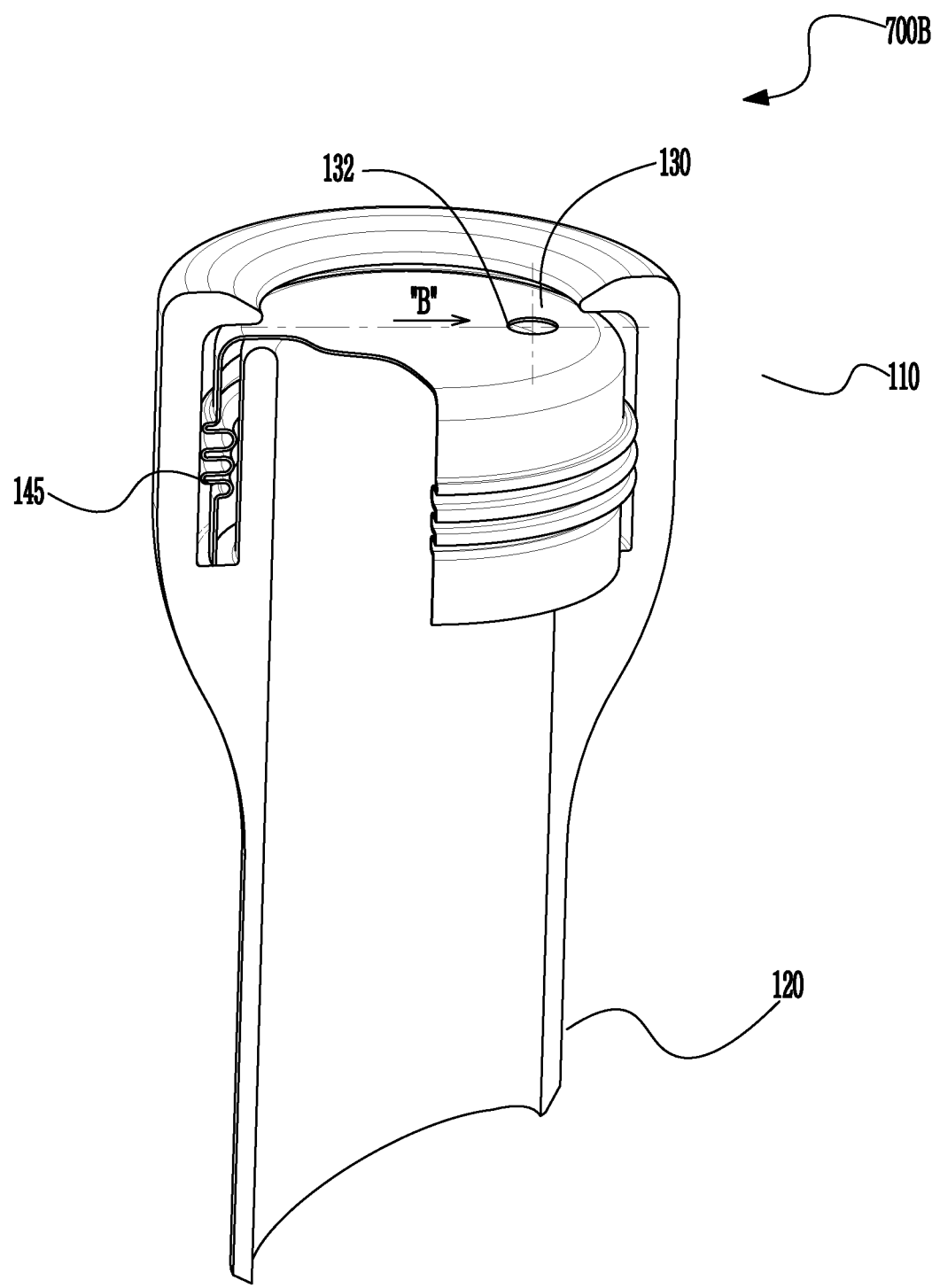
FIGS. 7B-7D are top perspective, partially cut-away views of the cannula and seal assemblies illustrating no rollers, and further depicting movement of the sealing member in various directions, in response to a surgical instrument inserted therethrough, in accordance with an embodiment of the present disclosure.
Figure 7C:
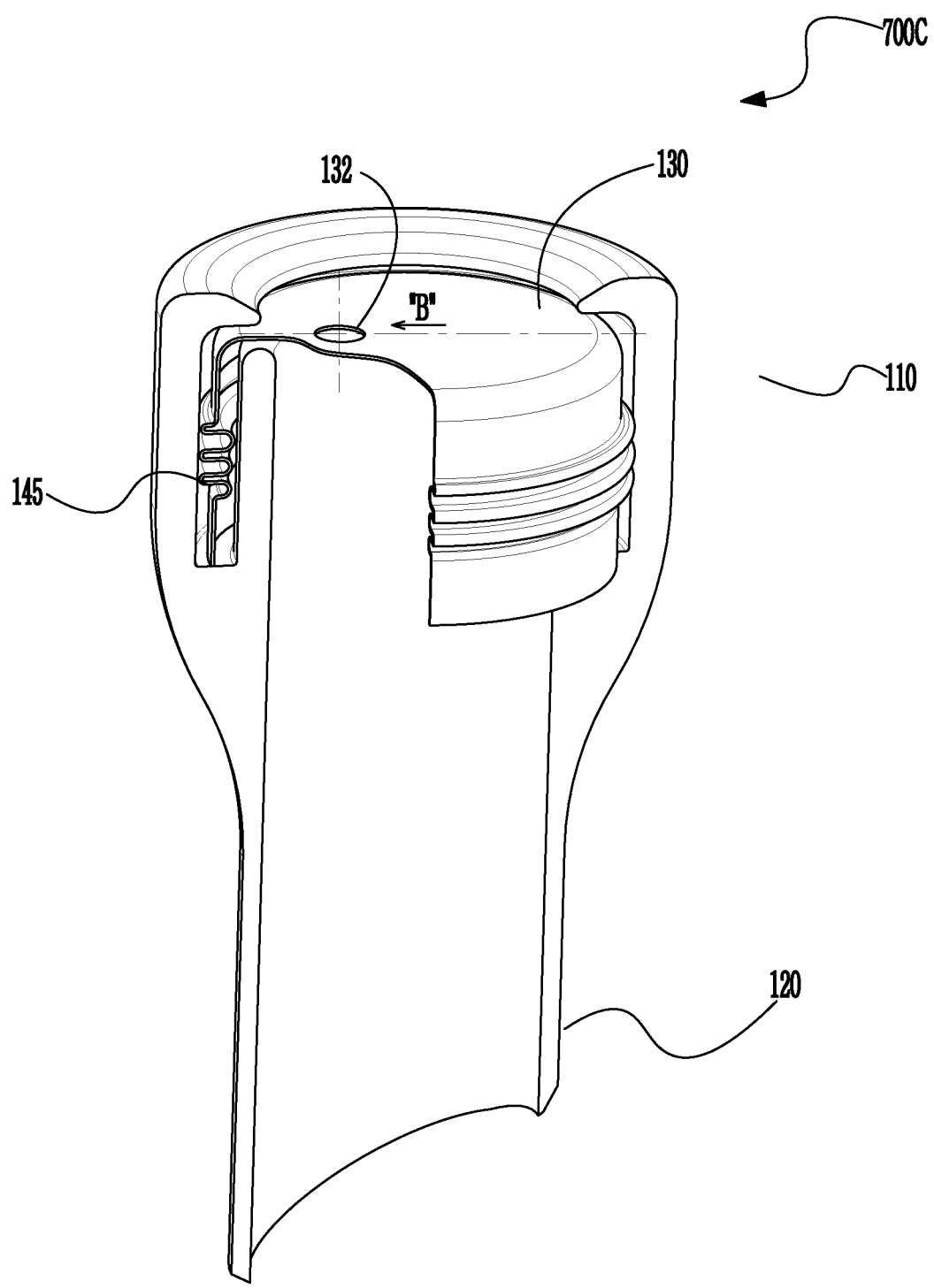
Figure 7D:
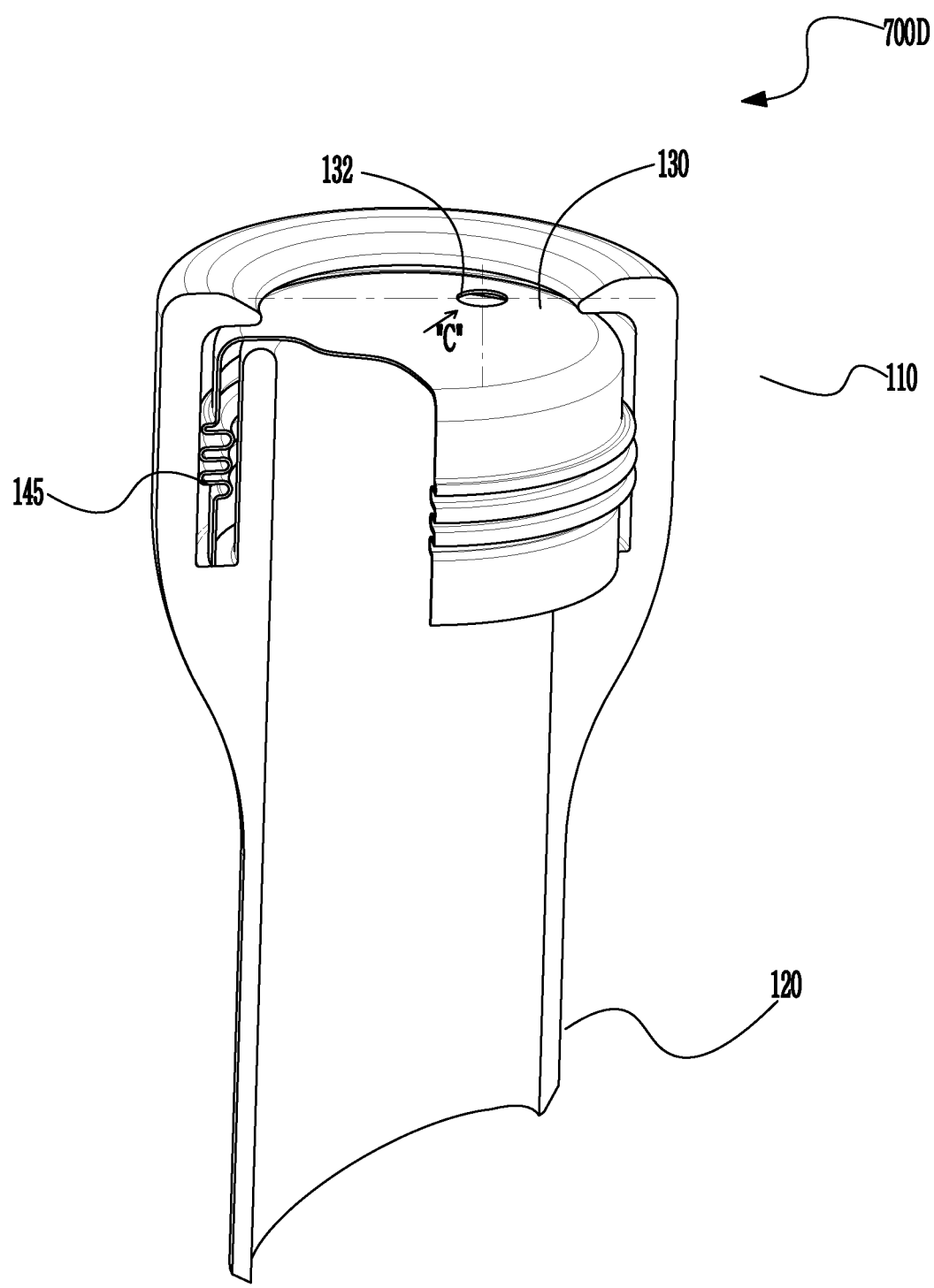

FIGS. 5-7D correspond to FIGS. 1-4D. However, in contrast to FIGS. 1-4D, FIGS. 5-7D do not include the roller assembly 140, 142. In other words, FIG. 5 is a side, cross-sectional view 500 of the cannula assembly 120 and the seal assembly 130, with a plurality of bellows members 145 and no rollers, whereas FIG. 6 is a side, cross-sectional view 600 of the cannula assembly 120 and the seal assembly 130 of FIG. 5, where the sealing member 130 is configured to receive at least one surgical instrument 160 therethrough. FIGS. 7A-7D depict the sealing member 130 in an unbiased position 700A, as well as a plurality of biased positions 700B, 700C, 700D, where movement of the sealing member 130 in a plurality of different directions (left, right, and diagonal) causes the plurality of bellows members 145 to be displaced/moved/biased. Therefore, it is contemplated that the plurality of rollers are optional. In this exemplary embodiment, the bellows members 145 may also be pre-loaded. In other words, once the surgical instrument 160 is removed from the opening 132 of sealing member 130, and after a shift has occurred, the bellows 145 are automatically re-positioned to their initial unbiased position.

In an alternative embodiment, the sealing member 130 may be frusto-conical in shape and define an aperture for sealed reception of the surgical instrument. In another alternative embodiment, sealing member 130 may be a flat disc-shaped valve, balloon valve, flapper valve, etc. The sealing member 130 may comprise a flat disc-shaped, conical, or hourglass-shaped member including a fabric material molded with an elastomer. In a further alternative embodiment, sealing member 130 may be a fabric seal and may be desirably arranged so as to have a constriction. A preferred material is a synthetic material such as nylon™, Kevlar™ or any other material that expands and compresses about an instrument inserted therethrough. The fabric may have a coating of urethane, silicon or other flexible lubricious materials to facilitate passage of an instrument or other object through the sealing member.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of presently disclosed embodiments. Thus the scope of the embodiments should be determined by the appended claims and their legal equivalents, rather than by the examples given.

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present disclosure. As well, one skilled in the art will appreciate further features and advantages of the present disclosure based on the above-described embodiments. Accordingly, the present disclosure is not to be limited by what has been particularly shown and described, except as indicated by the appended claims.

The invention claimed is:

1. A surgical access instrument for permitting access to body tissue, the surgical access instrument comprising:
   a housing having a proximal portion and a distal portion;
   a cannula member connected to the housing, the cannula member defining a longitudinal axis and permitting passage of a surgical object therethrough; and
   a sealing member disposed within the housing and including at least one opening therethrough, the sealing member connected to a plurality of bellows members located within a cavity defined by the housing, the cavity extending from the proximal portion to the distal portion of the housing such that the cavity is parallel to the longitudinal axis defined by the cannula member, wherein off-axis movement of the sealing member is enabled by a roller assembly circumferentially arranged at the proximal portion of the housing, the off-axis movement occurring in a plane perpendicular to the longitudinal axis defined by the cannula member.

2. The surgical access instrument according to claim 1, wherein the roller assembly is configured to include a first series of rollers circumferentially disposed on an inner rim of the housing and a second series of rollers circumferentially disposed on an outer rim of the housing, such that the first and second series of rollers cooperate to displace the sealing member.

3. The surgical access instrument according to claim 2,
wherein the first series of rollers are equally spaced apart from each other across a circumference of the inner rim of the proximal portion of the housing;
wherein the second series of rollers are equally spaced apart from each other across a circumference of the outer rim of the proximal portion of the housing; and
wherein the first series of rollers are disposed in opposed relation to the second series of rollers.

4. The surgical access instrument according to claim 1, wherein uneven displacement of the plurality of bellows members is caused when off-axis movement of the sealing member is enabled via a roller assembly.

5. The surgical access instrument according to claim 1, wherein when a portion of the plurality of bellows members are expanded on one portion of the housing, a portion of the plurality of bellows members on an opposed portion of the housing are contracted.

6. The surgical access instrument according to claim 1, wherein passage of the surgical object through the at least one opening of the sealing member causes off-axis movement of the sealing member.

7. The surgical access instrument according to claim 1, wherein each bellows member of the plurality of bellows members is biased to expand and/or contract based on off-axis movement of the sealing member when the surgical object is passed therethrough.

8. The surgical access instrument according to claim 7, wherein the at least one opening of the sealing member and the plurality of bellows members are in an initial unbiased position with the surgical object separated from the at least one opening of the sealing member.

9. The surgical access instrument according to claim 1, wherein the distal portion of the housing includes a duckbill seal configuration, the duckbill seal configuration including at least one slit for receiving the surgical object therethrough and maintaining the surgical object substantially parallel with respect to the longitudinal axis defined by the cannula member.

10. A surgical access instrument for permitting access to body tissue, the surgical access instrument comprising:
a housing having a proximal portion and a distal portion;
a cannula member connected to the housing, the cannula member defining a longitudinal axis and permitting passage of a surgical object therethrough; and
a sealing member disposed within the housing and including an opening therethrough, the sealing member connected to bellows members located within a cavity defined by the housing, the cavity extending from the proximal portion to the distal portion of the housing such that the cavity is parallel to the longitudinal axis defined by the cannula member, wherein uneven displacement of the bellows members is caused when off-axis movement of the sealing member is enabled via a roller assembly.

11. The surgical access instrument according to claim 10, wherein the roller assembly is configured to include first rollers circumferentially disposed on an inner rim of the housing and second rollers circumferentially disposed on an outer rim of the housing, such that the first and second rollers cooperate to displace the sealing member.

12. The surgical access instrument according to claim 11, wherein the rollers are equally spaced apart from each other across a circumference of the inner rim of the proximal end of the housing, the second rollers are equally spaced apart from each other across a circumference of the outer rim of the proximal end of the housing, and the first rollers are disposed in opposed relation to the second rollers.

13. The surgical access instrument according to claim 10, wherein expansion of a portion of the bellows members on one area of the housing results in contraction of a portion of the bellows members on an opposed area of the housing.

14. The surgical access instrument according to claim 10, wherein passage of the surgical object through the opening of the sealing member causes off-axis movement of the sealing member.

15. The surgical access instrument according to claim 10, wherein each bellows member is biased to expand and/or contract based on off-axis movement of the sealing member when the surgical object is passed therethrough.

16. The surgical access instrument according to claim 15, wherein the opening of the sealing member and the bellows members are in an initial, unbiased position with the surgical object separated from the opening of the sealing member.

17. The surgical access instrument according to claim 10, wherein the distal portion of the housing includes a duckbill seal configuration, the duckbill seal configuration including a slit for receiving the surgical object therethrough and maintaining the surgical object substantially parallel with respect to the longitudinal axis defined by the cannula member.

* * * * *